(12) United States Patent
Bulliard et al.

(10) Patent No.: US 6,861,535 B2
(45) Date of Patent: Mar. 1, 2005

(54) CYCLIZATION METHOD FOR THE SYNTHESIS OF PYRROLIDINE DERIVATIVE COMPOUNDS

(75) Inventors: Michel Bulliard, Angers (FR); Blandine Laboue, Angrie (FR); Jean-Francois Pluvie, Angers (FR); Sonia Roussiasse, Ecouflant (FR); Tony Pintus, Bouchemaine (FR)

(73) Assignee: PPG-SIPSY (FR)

( * ) Notice: Subject to any disclaimer, the term of this patent is extended or adjusted under 35 U.S.C. 154(b) by 0 days.

(21) Appl. No.: 10/449,377

(22) Filed: May 30, 2003

(65) Prior Publication Data

US 2004/0034235 A1 Feb. 19, 2004

Related U.S. Application Data

(63) Continuation of application No. PCT/FR01/03796, filed on Nov. 30, 2001.

(30) Foreign Application Priority Data

Dec. 1, 2000 (FR) .............................................. 00 15626

(51) Int. Cl.$^7$ ............................................ C07D 207/00
(52) U.S. Cl. .................................................... 548/541
(58) Field of Search ...................... 548/541; 546/184; 540/484

(56) References Cited

U.S. PATENT DOCUMENTS 5,144,042 A * 9/1992 Seido et al. ................. 548/541

FOREIGN PATENT DOCUMENTS

| EP | 0 452 143 A | 10/1991 |
| JP | 60 104061 | 3/1985 |

* cited by examiner

Primary Examiner—Joseph K. McKane
Assistant Examiner—Robert Shiao
(74) Attorney, Agent, or Firm—DLA Piper Rudnick

(57) ABSTRACT

A method for preparing pyrrolidine derivatives comprising cyclizing a compound of formula (I):

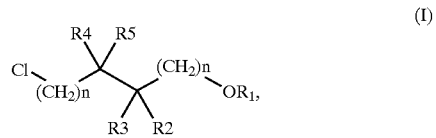

in the presence of: a) a catalyst, b) a primary amine and c) a base, in a solvent to obtain pyrrolidine derivative of formula (II) below:

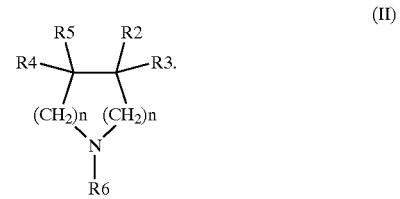

9 Claims, 1 Drawing Sheet

CYCLIZATION METHOD FOR THE SYNTHESIS OF PYRROLIDINE DERIVATIVE COMPOUNDS

RELATED APPLICATION

This is a continuation of International Application No. PCT/FR01/03796, with an international filing date of Nov. 30, 2001, which is based on French Patent Application No. 00/15626, filed Dec. 1, 2000.

FIELD OF THE INVENTION

This invention pertains to a method for the preparation of optically active or nonactive substituted pyrrolidine derivates.

BACKGROUND

Optically active or nonactive substituted pyrrolidine compounds are essential intermediaries for the synthesis of pharmaceutically active ingredients. Preparation of optically active or nonactive substituted pyrrolidine compounds requires at least four synthesis steps.

One method of preparing these compounds is envisaged, for example, by European patent EP 452143 in the name of TAKASAGO. This method discloses the preparation of a 1-benzyl-3-hydroxypyrrolidine compound via a cyclization reaction of an intermediary compound, 4-chloro,3-hydroxy-1-methylsulfonyloxy-butane, with the compound benzylamine in the presence of sodium carbonate in ethanol.

SUMMARY OF THE INVENTION

This invention relates to a method for preparing pyrrolidine derivatives comprising cyclizing a compound of formula (I):

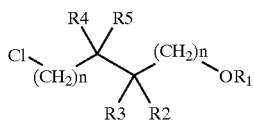

wherein $R_1$ represents a mesyl group, a tosyl group, a nosyl group or a trityl group; $R_2$ and $R_4$, which can be the same or different, represent a hydrogen atom, a halogen atom, a hydroxyl group, an alkyloxy group, an aryloxy group, a mesyl group, a tosyl group, a nosyl group, a trityl group, an alkyl group or together represent a double bond; $R_3$ and $R_5$, which can be the same or different, represent a hydrogen atom, a halogen atom, a hydroxyl group, an alkyloxy group, an aryloxy group, a mesyl group, a tosyl group, a nosyl group, a trityl group, an alkyl group or together represent a saturated or unsaturated $C_{3-9}$ cycloalkyl group or a $C_{5-10}$ aryl group, said cycloalkyl or aryl groups are optionally substituted by a $C_{1-5}$ alkyl group, a halogen atom, a hydroxy group, a $C_{1-5}$ alkoxy group and optionally have one or more heteroatoms selected from the group consisting of O, N, S and Si; and n is a whole number of 1, 2 or 3, in the presence of: a) a catalyst, b) a primary amine of formula $R_6NH_3$ wherein $R_6$ represents a hydrogen atom, an alkyl group, an aryl group or an alkylaryl group and c) a base, in a solvent to obtain pyrrolidine derivative of formula (II) below:

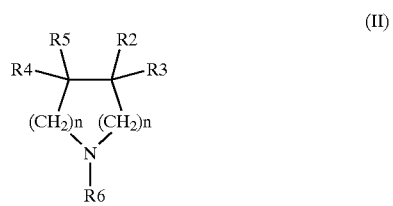

wherein $R_2$, $R_3$, $R_4$ $R_5$ and n have the same meanings as in formula (I) and $R_6$ represents a hydrogen atom, an alkyl group, an aryl group or an alkylaryl group.

DETAILED DESCRIPTION

Figure 1:
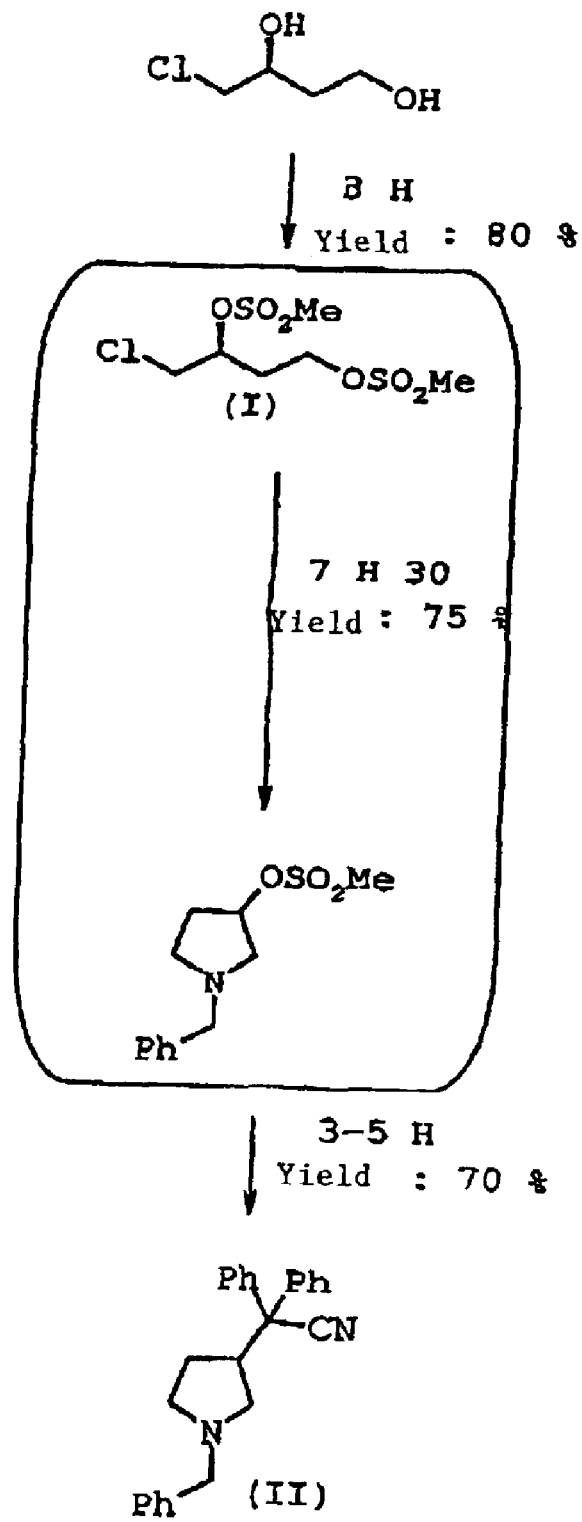
FIG. 1 shows schematically the production of the intermediary compound of formula (I) and the method for the preparation—by cyclization of this compound—of the substittued pyrrolidine derivative of formula (II).

We have developed a new method for preparing optically active or nonactive substituted pyrrolidine derivatives comprising a cyclization reaction which employs a catalyst and does not require the conventional use of intermediary hydroxylated pyrrolidine derivative compounds. The number of steps in the preparation procedure is thereby reduced. Moreover, the method of the invention makes it possible to obtain said derivatives with very high yields and to thereby decrease the manufacturing costs.

The invention thus provides a method for preparing pyrrolidine derivatives comprising a cyclization reaction of a compound of formula (I) below:

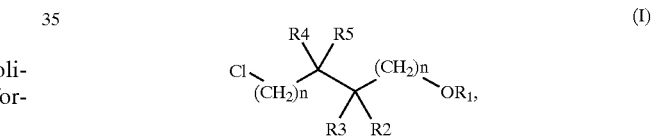

wherein $R_1$ represents a mesyl group, a tosyl group, a nosyl group or a trityl group, $R_2$ and $R_4$, which can be the same or different, represent a hydrogen atom, a halogen atom, a hydroxyl group, an alkyloxy group, an aryloxy group, a mesyl group, a tosyl group, a nosyl group, a trityl group, an alkyl group or together represent a double bond, $R_3$ and $R_5$, which can be the same or different, represent a hydrogen atom, a halogen atom, a hydroxyl group, an alkyloxy group, an aryloxy group, a mesyl group, a tosyl group, a nosyl group, a trityl group, an alkyl group or together represent a saturated or unsaturated $C_{3-9}$ cycloalkyl group or a $C_{6-10}$ aryl group, said cycloalkyl or aryl groups are optionally substituted by a $C_{1-5}$ alkyl group, a halogen atom, a hydroxy group, a $C_{1-5}$ alkoxy group and optionally have one or more heteroatoms such as O, N, S and Si, and n is a whole number of 1, 2 or 3, in the presence of a) a catalyst.

b) a primary amine of formula $R_6NH_3$ wherein $R_6$ represents a hydrogen atom, an alkyl group, an aryl group or an alkylaryl group and c) a base, in a solvent to obtain the pyrrolidine derivative of formula (II) below:

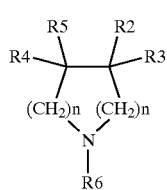

wherein $R_2$, $R_3$, $R_4$ $R_5$ and n have the same meanings as in formula (I) and $R_6$ represents a hydrogen atom, an alkyl group, an aryl group or an alkylaryl group.

According to a preferred embodiment, the catalyst is selected from an alkali metal halide, an ammonium halide or a phosphonium halide. Most preferably, the catalyst is selected from among a sodium iodide or bromide, a lithium iodide or bromide, a potassium iodide or bromide, a cesium iodide or bromide, a rubidium iodide or bromide, an ammonium or phosphonium iodide or bromide, selected from among an ammonium iodide or bromide, a phenyltrimethylammonium iodide or bromide, tetrabutylammonium iodide or bromide, benzylammonium iodide or bromide, trimethylammonium iodide or bromide, triphenylphosphine iodide or bromide, a triphenylphosphine dibromide, a triphenylphosphite dibromide or a potassium fluoride.

The method of the invention advantageously comprises a reaction of cyclization of a compound of formula (I) in which $R_1$ represents a mesylate group, $R_2$ represents a mesylate group and $R_3$, $R_4$ and $R_5$ each represent a hydrogen atom to obtain a pyrrolidine derivative of formula (II) in which $R_2$ represents a mesylate group, $R_3$, $R_4$ and $R_5$ each represent a hydrogen atom and $R_6$ represents a benzyl group.

According to a preferred embodiment, the base is selected from among triethylamine, pyridine, piperidine, NaOH, NaHCO₃, KOH, KHCO₃ or a carbonate selected from among sodium carbonate, lithium carbonate, potassium carbonate, cesium carbonate or rubidium carbonate.

The method of the invention can be carried out in the presence of any suitable solvent capable of dissolving the substrate and not affecting the reaction. The solvent can be used individually or as part of a mixture. The method of the invention is preferably implemented in the presence of any solvent selected from among water, a hydrocarbon such as hexane, heptane, octane, nonane, decane, benzene, toluene and xylene, an ether such as tetrahydrofuran, dioxane, dimethoxyethane, diisopropyl ether and diethylene glycol dimethyl ether, an ester such as ethyl acetate, butyl acetate and ethyl propionate, a ketone such as acetone, diisopropyl ketone, methylisobutyl ketone, methylethyl ketone and acetylacetone, an alcohol such as methanol, ethanol, n-propanol and iso-propanol, a nitrile such as acetonitrile, an alkyl halide such as dichloromethane, chloroform and 1,2-dichloroethane, an amine such as triethylamine, diisobutylamine, N-methylpiperidine, ethyldiisopropylamine, N-methylcyclohexylamine and pyridine, an organic acid such as acetic acid, propionic acid and formic acid, an amide such as formamide, N,N-dimethylformamide, a sulfoxide such as dimethylsulfoxide, alone or in mixture.

The method of the invention most preferably employs as the solvent: water, acetonitrile, methanol, ethanol, n-propanol, iso-propanol, acetone, diisopropyl ketone, methylisobutyl ketone, methylethyl ketone, acetylacetone, formamide, N,N-dimethylformamide, dimethylsulfoxide, tetrahydrofuran, dioxane, dimethoxyethane, diisopropyl ether or diethylene glycol dimethyl ether, alone or in mixture.

The amount of catalyst used in relation to the amount of compound of formula (I) is advantageously comprised between about 0.1% and about the stoichiometric amount.

The cyclization reaction according to the method of the invention is advantageously performed at a temperature comprised between about 10° C. and about the reflux temperature of the solvent.

The duration of the cyclization reaction of the method of the invention is generally greater than or equal to about 1 hour. As a function of the nature of the compound of formula (I), the duration is, for example, between about 1 hour and about 70 hours.

The invention also includes the use of a catalyst in a method for the preparation of a compound of formula (II) from a compound of formula (I).

According to a preferred embodiment, the invention uses a catalyst selected from among an alkali metal halide, an ammonium halide or a phosphonium halide in a procedure for the preparation of a compound of formula (I) from a compound of formula (II).

Most preferably the invention uses a catalyst selected from among a sodium iodide or bromide, a lithium iodide or bromide, a potassium iodide or bromide, a cesium iodide or bromide, a rubidium iodide or bromide, an ammonium iodide or bromide, a phenyltrimethylammonium iodide or bromide, a tetrabutylammonium iodide or bromide, a benzylammonium iodide or bromide, a triphenylphosphine dibromide, a triphenylphosphite dibromide or a potassium fluoride in a procedure for the preparation of a compound of formula (II) from a compound of formula (I).

The invention will be better comprehended by referring to the examples below which illustrate in a nonlimitative manner the method for the preparation of substituted pyrrolidine derivatives according to aspects of the invention.

EXAMPLE 1

Preparation of 4-chloro-1,3-butanediol, dimethanesulfonate ester (S).

2.2 kg (17.66 moles) of 4-chloro-1,3-butanediol, 20 l of THF and 3.746 kg (37.086 moles) were introduced into a 50-l reactor. The medium was chilled to about 10° C. (±3° C.). Then, 4.044 kg (35.32 moles) of methanesulfonyl chloride were introduced while maintaining the temperature of the reaction medium at 10° C. (±3° C.). The reaction medium was maintained at a temperature of 22° C. (±3° C.) for 12 hours. The reaction medium was chilled to 10° C. (±3° C.) and 6.4 l of a 36% solution of hydrochloric acid was added. The reaction medium was maintained for one hour at 22° C. (±3° C.). It was then extracted 3 times with 4.4 l of toluene. The organic phases were concentrated.

This yielded 5.075 kg of product at 78.2% chemical purity.

Yield: 80%.

$^1$H NMR spectrum:

4.9 to 5.0 ppm (m, 1H, CH(OSO₂Me)); 4.4 to 4.3 ppm (m, 2H, CH₂(OSO₂Me)); 3.7 to 3.8 ppm (m, 2H, CH₂Cl); 3.1 ppm (s, 3H, CH₃); 3.0 ppm (s, 3H, CH₃); 2.24 to 2.18 ppm (m, 2H, CH₂).

$^{13}$C NMR spectrum:

77–76 ppm (—C(OSO₂Me)—); 64 ppm (CH₂(OSO₂Me)); 45 ppm (CH₂Cl); 38–36.9 ppm (CH₃ of OSO₂Me); 31 ppm (CH₃).

EXAMPLE 2

Preparation of 3-pyrrolidinol,1-(phenylmethyl)-, methanesulfonate (ester), (S)—

7.8 g (0.028 mol) of the product obtained in example 1, 40 ml of THF, 11.82 g (0.084 mole) of K₂CO₃, 0.94 g (5.7

10$^{-3}$ mole) of potassium iodide, 3.97 g (0.0364 mole) of benzylamine and 15 ml of water were introduced into a 250 ml-flask. The reaction medium was heated at reflux for 7 hours 30 minutes. Then 20 ml of toluene was added and the precipitate was filtered. After decantation, the filtrate was extracted with 15 ml of toluene. The toluene phases were concentrated.

9.5 g of product was obtained.

Yield: 77.5%.

$^{1}$H NMR spectrum:

7.25 ppm (m, 5H, H arom.); 5.1 to 5.2 ppm (m, 1H, CH); 3.7 to 3.55 ppm (m, 2H, NCH$_3$Ph); 2.95 ppm (s, 3H, CH$_3$); 2.7–1.95 ppm (m, 6H, CH$_2$ pyrrolidine).

$^{13}$C NMR spectrum:

118 ppm (C arom.); 128 ppm (C arom.); 80 ppm (CH (OSO$_2$Me); 59 ppm (NCH$_2$Ph); 52 ppm (NCH2); 38 ppm (CH$_3$); 32 ppm (CH$_2$).

What is claimed is:

1. A method for preparing pyrrolidine derivatives comprising cyclizing a compound of formula (I):

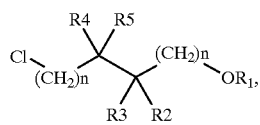

(I)

wherein R$_1$ represents a mesyl group, a tosyl group, a nosyl group or a trityl group, R$_2$ and R$_4$, which can be the same or different, represent a hydrogen atom, a halogen atom, a hydroxyl group, an alkyloxy group, an aryloxy group, a mesyl group, a mesylate group, a tosyl group, a nosyl group, a trityl group, an alkyl group or together represent a double bond, R$_3$ and R$_5$, which can be the same or different, represent a hydrogen atom, a halogen atom, a hydroxyl group, an alkyloxy group, an aryloxy group, a mesyl group, a tosyl group, a nosyl group, a trityl group, an alkyl group or together represent a saturated or unsaturated C$_{3-9}$ cycloalkyl group or a C$_{5-10}$ aryl group, said cycloalkyl or aryl groups are optionally substituted by a C$_{1-5}$ alkyl group, a halogen atom, a hydroxy group, a C$_{1-5}$ alkoxy group and n is a whole number of 1, in the presence of:
  a) a catalyst.
  b) a primary amine of formula R$_6$NH$_3$
  wherein R$_6$ represents a hydrogen atom, an alkyl group, an aryl group or an alkylaryl group and
  c) a base,
in a solvent to obtain pyrrolidine derivative of formula (II) below:

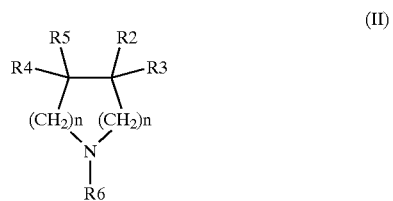

(II)

wherein R$_2$, R$_3$, R$_4$ R$_5$ and n have the same meanings as in formula (I) and R$_6$ represents a hydrogen atom, an alkyl group, an aryl group or an alkylaryl group.

2. The method according to claim 1, wherein the catalyst is selected from the group consisting of an alkali metal halide, an ammonium halide and a phosphonium halide.

3. The method according to claim 1, wherein the catalyst is selected from the group consisting of a sodium iodide or bromide, a lithium iodide or bromide, a potassium iodide or bromide, a cesium iodide or bromide, a rubidium iodide or bromide, an ammonium iodide or bromide, a phenyltrimethylammonium iodide or bromide, a tetrabutylammonium iodide or bromide, a benzylammonium iodide or bromide, a triphenylphosphine dibromide, a triphenylphosphite dibromide and a potassium fluoride.

4. The method according to claim 1, wherein, in formula (I), R$_1$ represents a mesyl group, R$_2$ R$_3$, and R$_5$ independently represent hydrogen atom, R$_4$ represents a mesylate group and, in formula (II), R$_4$ represents a mesyl group, R$_2$, R$_3$, and R$_5$ each represent a hydrogen atom and R$_6$ represents a benzyl group.

5. The method according to claim 1, wherein the base is selected from the group consisting of triethylamine, pyridine, piperidine, NaOH, NaHCO$_3$, KOH, KHCO$_3$, sodium carbonate, lithium carbonate, potassium carbonate, cesium carbonate and rubidium carbonate.

6. The method according to claim 1, wherein the solvent is selected from the group consisting of water, acetonitrile, methanol, ethanol, n-propanol, iso-propanol, acetone, diisopropyl ketone, methylisobutyl ketone, methylethyl ketone, acetylacetone, formamide, N,N-dimethylformamide, dimethylsulfoxide, tetrahydrofuran, dioxane, dimethoxyethane, diisopropyl ether, diethylene glycol dimethyl ether and mixtures thereof.

7. The method according to claim 1, wherein the amount of catalyst in relation to the amount of compound of formula (I) is between about 0.1% and about a stoichiometric amount.

8. The method according to claim 1, wherein the cyclization is performed at a temperature between about 10° C. and about the reflux temperature of the solvent.

9. The method according to claim 1, wherein the duration of cyclization is between about 1 hour and about 70 hours.

* * * * *